(12) United States Patent
Schwartz, Jr.

(10) Patent No.: US 8,753,876 B2
(45) Date of Patent: Jun. 17, 2014

(54) ENERGY RECOVERY SYSTEM (76) Inventor: Andrew K. Schwartz, Jr., Manvel, TX (US)

( * ) Notice: Subject to any disclaimer, the term of this patent is extended or adjusted under 35 U.S.C. 154(b) by 748 days.

(21) Appl. No.: 12/404,833

(22) Filed: Mar. 16, 2009

(65) Prior Publication Data

US 2009/0229595 A1    Sep. 17, 2009

Related U.S. Application Data

(60) Provisional application No. 61/036,488, filed on Mar. 14, 2008.

(51) Int. Cl.
*B65D 88/12* (2006.01)
*C12M 1/00* (2006.01)
*F24H 1/00* (2006.01)
*F28D 21/00* (2006.01)

(52) U.S. Cl.
CPC .................................... *F28D 21/001* (2013.01)
USPC .................. 435/289.1; 435/262.5; 435/290.1; 210/175; 210/259; 210/603; 210/612

(58) Field of Classification Search
CPC ...................................................... F28D 21/001
USPC .................. 126/344; 435/289.1, 290.1, 262.5
See application file for complete search history.

(56) References Cited

U.S. PATENT DOCUMENTS

| | | | |
|---|---|---|---|
| 2,756,035 A * | 7/1956 | Axelrad et al. | 299/6 |
| 3,428,557 A * | 2/1969 | Rivers | 210/746 |
| 4,948,511 A * | 8/1990 | Swanson et al. | 210/634 |
| 5,050,375 A * | 9/1991 | Dickinson | 60/39.12 |
| 2005/0067348 A1* | 3/2005 | Logan et al. | 210/609 |
| 2007/0095734 A1* | 5/2007 | Lee, Jr. | 210/180 |

OTHER PUBLICATIONS

Derwent abs of Matsumoto (JP 58-115222); Jul. 1983.*

* cited by examiner

*Primary Examiner* — Michael Marcheschi
*Assistant Examiner* — Shanta G Doe
(74) *Attorney, Agent, or Firm* — Conley Rose, P.C.

(57) ABSTRACT

An apparatus and method for recovering thermal energy from boiler stack exhaust gases and using the thermal energy in biomaterial processing. The apparatus and method include means to improve the boiler's operation and reduce emission of certain regulated compounds.

12 Claims, 7 Drawing Sheets

ENERGY RECOVERY SYSTEM

CROSS-REFERENCE TO RELATED APPLICATIONS

This application claims benefit of U.S. Provisional Application Ser. No. 61/036,488 filed on Mar. 14, 2008, entitled "Energy Recovery System" which is hereby incorporated herein by reference in its entirety.

STATEMENT REGARDING FEDERALLY SPONSORED RESEARCH OR DEVELOPMENT

Not applicable.

BACKGROUND OF THE INVENTION

1. Field of the Invention

This invention relates to the field of energy recovery. More specifically, the invention relates to a method of recovering and recycling thermal energy from industrial and utility boiler applications.

2. Background of the Invention

Ethanol-based fuel production and industrial fermentation processes rely heavily upon the conversion of food crops to fuel or other chemicals. Corn, sugar beets, sugarcane, and other crops are regularly used as sources of starch or sugar. Implementation of crop-based feedstocks for ethanol fuels has negative implications in the global food stocks. Additionally, the temperate climate zones where these crops are primarily grown undergo seasonal changes that prevent the year round regular production of ethanol fuel demanded by industry and transportation.

Cellulose is a major structural component of nearly every plant, making it one of the most abundant molecules on the planet. Biomacromolecular cellulose consists of glucose monomers. Algin is a structural polysaccharide in the cell walls of marine plants. The biomacromolecule algin consists of D-mannuronate epimers. Furthermore, as a plant-produced material, both are easily renewable resources that do not require starch or sugar-rich food crops. The capacity to break them down into monomers yields an extensive supply of sugars for ethanol, other fermentation or other chemical syntheses. The primary difficulty with cellulose and algin is that it is difficult to hydrolyze to obtain the sugar monomers because the polymer is protected by a number of other biomaterials.

Hydrolytic techniques currently exist to hydrolyze cellulose to produce sugars. However, available technologies require costly physical plants and the infrastructure to operate them. The significant capital expenditure is a strong incentive for the avoidance of a company's investment in new plants or technologies for the exclusive production of fuel grade ethanol by processing of plant-based biomaterial. Further, the power supply industry is facing strict regulations on emissions produced from the burning of fossil fuels. Power plants are being required to add components and facilities such as treatment facilities, filters, heat exchangers, stack scrubbers, and energy capturing components to remove certain waste products and recycle energy released by the system. These additional facilities and components are required to lower the nitrogen oxide, sulfur, and mercury emissions to meet new regulations.

Power plant systems typically include boilers to produce steam for the process of the power plant system and often the waste heat from the boilers is lost and not recovered or recycled for reuse in the power plant system or other related process system. Consequently, there is a need for the recovery and recycling of the thermal energy from the burning of fossil fuels in the power plant system and using that thermal energy for the processing of biomaterials.

BRIEF SUMMARY

A method of operating a thermal recycling system includes transporting thermal energy and products from a boiler, a cooker and a bioreactor through the system whereby the thermal energy from the boiler is used to process biomaterial, and thermal energy from biological processes is used to preheat combustion air. The method also reduces emissions and recovers heat by returning gases from the biomaterial processing to the boiler. This is accomplished utilizing low level heat from bioprocesses and other sources to humidify combustion air, then taking advantage of the additional humidity supplied by products of combustion and/or fuel associated water to dehumidify the stack gas by a comparable amount but at a higher temperature. The temperature difference between humidification and dehumidification is sufficient to allow a heat exchanger to transfer the heat of dehumidification to the incoming combustion air. Condensate from dehumidification of stack gas is usually acidic and may be used for neutralization or for dilute acid hydrolysis or pretreatment of cellulose and/or algin.

A boiler energy recycling system comprises a boiler, a cooker, a bioreactor, a combustion air preheater and a water treatment facility. The hot gases from the boiler are directed to the cooker and warmed combustion air is directed to the bioreactor, the cooker for pulping or otherwise favorably altering the properties of the biomaterial and the bioreactor for aerobically, or anaerobically treating biomaterial. The water treatment facility treats the water flowing into the boiler and provides its wastewater to the cooker. The water treatment facility can also produce treated water for the cooker or for other purposes.

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION

Figure 1:
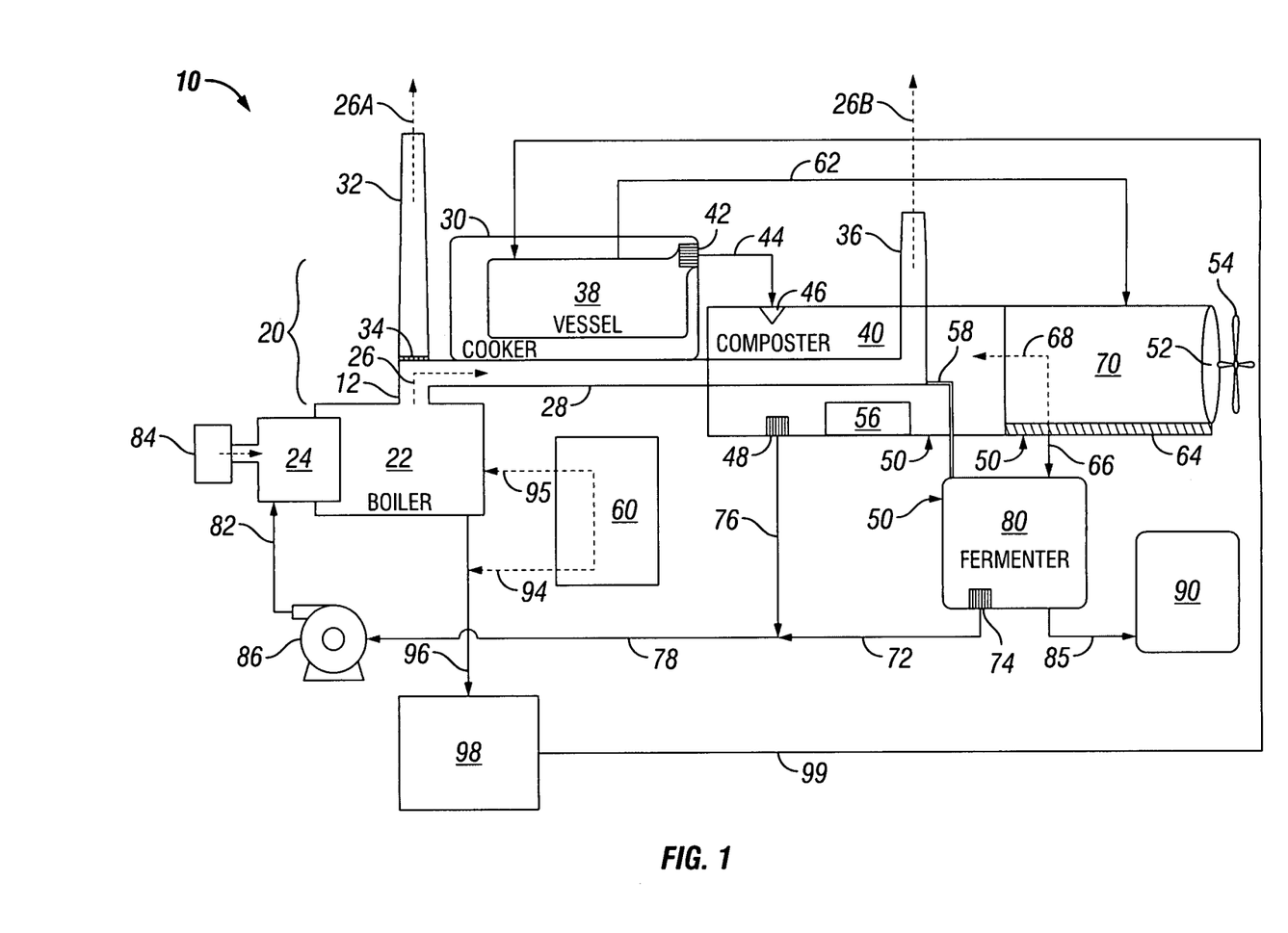
FIG. 1 is a schematic illustrating an embodiment of an energy recovery and recycling system.

FIG. 1 is a schematic illustrating an embodiment of an energy recovery and recycling system 10. Energy recovery and recycling system 10 comprises a stack gas system 20 having a boiler 22 with a burner 24 that produces a stack gas 26 that supplies thermal energy, via a conduit 28, to a biomaterial cooker facility 30 and a composter 40 of a bioreactor 50. Bioreactor 50 may also comprise a biomaterial separator 70 and fermenter 80. The energy recovery and recycling system 10 is a supplemental system to a conventional boiler 22 application used in another plant process. The boiler may create steam or thermal energy for such other processes. Additionally, the boiler operation wastewater may be used in other processes.

The water flowing through the tubes of boiler 22 is heated by burner 24 that combusts a hydrocarbon or fossil fuel such as natural gas, coal, or oil from feed 84 mixed with a combustion air from feed 82. The stack gas system 20 may further include an air blower 86 which introduces the combustion air feed 82 into burner 24. The flue gas produced by burner 24 exits an outlet 12 of boiler 22 that is connected to a first stack 32. A boiler water-treatment facility 60 may provide water treated to remove inorganic and metallic contaminants from the boiler feedwater for the boiler 22.

A damper 34 positioned within stack 32 reversibly closes stack 32 to the passage of flue gases 26a through stack 32. Damper 34 serves to direct the remainder of the stack gases 26 into conduit 28. In further applications, the damper 34 improves safety of the stack during maintenance and startup. Conduit 28 passes adjacent to biomaterial cooker facility 30 and passes through composter 40. Conduit 28 releases stack gas 26b through a second stack 36 to the environment.

Biomaterial cooker facility 30 is located in proximity to boiler 22 along and/or adjacent to conduit 28. Biomaterial cooker facility 30 may be a widening or a broadening in the conduit 28. Biomaterial cooker facility 30 cooks ligno-cellulose rich biomaterial and/or algin rich biomaterial at high temperature. Biomaterial cooker facility comprises a vessel 38 for holding the biomass under high temperature and may be moveable within cooker facility 30 relative to stack gas conduit 28 whereby the temperature within the vessel 38 may be regulated by the proximity of vessel 38 to the stack gas conduit 28. In stationary cooker embodiments, dampers may be located in conduit 28 to direct and route gas to and from cooker facility 30 as a means to regulate temperature in vessel 38. Vessel 38 further comprises at least one vent 42 for removing and directing gases resulting from the cooking of biomass to conduit 44. Composter 40 includes an inlet 46 in communication with vent 42 of vessel 38. In alternative embodiments, biomaterial cooker facility 30 and composter 40 are located in the same building and on opposite sides of gas conduit 28.

Bioreactor 50 comprises composter 40, biomaterial separator 70, and fermenter 80. In embodiments, composter 40 and separator 70 are constructed as portions of the same building. Bioreactor 50 comprises at least one air intake system 52 having a fan 54 for blowing air over/through biomaterial separator 70 and the composter 40. Bioreactor 50 comprises at least one outlet 48 for withdrawing the heated air from the bioreactor and communicates with composter gas conduit 76 into blower feed conduit 78 to produce a combustion air stream 82 returning it to burner 22. Outlet 48 is preferably located in composter 40 and configured to maintain an air pressure inside composter 40 such that it is at least below ambient pressure.

Composter 40 is constructed as a heat exchanger for the removal of heat from gas conduit 28 to heat aerobically composting biomaterial. Composter 40 is configured as a generally open room facility with stack gas conduit 28 running substantially therethrough. Composter 40 can be open to the environment at one end. The walls of composter 40 are thermally insulated and corrosion resistant. For example, the walls of composter 40 may be constructed of materials such as glass, ceramic or plastic. Composter 40 may include at least one industrial or commercial garage bay 56 configured to permit hoppers, trucks, rail cars, or other similar transportation vehicles access to the interior of the composter 40.

The composter 40 serves the purpose of making a useful product from lignin and other portions of the biomass not contained in the desired primary cooker product. These portions do not remain with the pulp or other desired cooker product, nor degrade in the fermenter 80. Composter feed may include additional biomaterials such as, but not limited to, residential yard waste, commercial crop processing waste or commercial building site plant clearings. Furthermore, any biomass rejected from the cooker feed for oversize, undersize, excess associated dirt or any other reason will be transported to the composter 40. Composting is the aerobic decomposition of organic matter. Heat from gas conduit 28 is favorable for the organisms responsible for the process of composting. Additionally, hot vapors from the vessel 38 are passed into the composter 40. The process of composting produces some volatile, organic gas. This composter gas 76 includes water vapor, methane, and nitrogenous gases. Additionally, during heating of compost in composter 40, the gas conduit 28 may cool below the dew point of some vapors in the gas. The condensate supplements the water and may be used to balance the alkalinity in the fermenter 80. In other embodiments condensate from the gas conduit 28 may be used for acidic cooking liquor or the dilute acid hydrolysis of biomass when the fossil fuel fired includes a sulfur component. Condensate exits from the gas conduit 28 at outlet 58 and is drained to anaerobic fermenter 80. The biomaterial separator 70 may be a portion of composter 40. The biomaterial separator 70 comprises a separation facility for the product stream 62 of biomaterial cooker facility 30. Solid biomaterial leftover from cooking in biomaterial cooker facility 30 is hereinafter referred to as pulp. The liquid the biomaterial heated in the biomaterial cooker facility 30 is referred to as cooking liquor. However, one skilled in the art will recognize that many potential cooker applications result in additional solid or liquid products. Product stream 62 includes pulp and cooking liquor.

The biomaterial separator 70 separates the pulp from the cooking liquor by flowing the product stream 62 over a solid/liquid separation device known to those skilled in the art. Additional products, if any, may be separated as well. The liquid and finely divided solid portion not recovered with the pulp flows into a drain 64. Cooking liquor from biomaterial separator 70 flows through drain 64 and into conduit 66 connected to fermenter 80 for fermenting. Pulp from separator 70 may be transported offsite for ethanol or other fermentation. On site, the pulp may be transported by a biomaterial vessel conduit 68 or other means to composter 40 for bio-processing. The bio-processing steps may comprise fungal pretreatment or enzyme production. In some embodiments, the vapors from the biomaterial separator are passed through the composter 40 to heat and humidify the combustion air. The cooking liquor is directed through outlet 66 into fermenter 80.

Fermenter 80 may be a conventional fermenter known by one skilled in the art for fermenting a liquid having dissolved biomaterials. In certain embodiments, fermenter 80 is an anaerobic methane fermenter. Fermenter 80 receives cooking liquor from bioreactor 50 and condensate from stack gas conduit 28 through outlet 58 for processing. Fermenter 80 produces gases and water. The fermenter gases are recycled to boiler 22 by conduit 72 and the water is drained to a water treatment facility 90 for removing biomaterial contaminants.

The fermenter 80 breaks down the biomaterial suspended in the cooking liquor and condensate without oxygen. Fermentation may create a methane and volatile organic gas mixture. This fermenter gas from fermentation of the cooking liquor is removed from fermenter 80 via fermenter gas outlet 74 to gas conduit 72. Fermenter gas conduit 72 communicates with composter gas conduit 76 into blower feed conduit 78 to produce a combustion air stream 82. Combustion air stream 82 may be transported via blower 86.

Further waste compounds may be removed from the liquid from separation facility 70 and fermenter 80 by any means known to one of skill in the art. In embodiments, the liquid is drained from fermenter 80 to a treatment facility 90. The water treatment facility 90 may comprise any known to one skilled in the art. In certain embodiments, water treatment facility 90 is a trickling filter. A trickling filter acts as an attached growth bioreactor and a settler to remove organic compounds from water. In energy recovery system 10, water treatment facility 90 releases water of sufficient purity to discharge. In some arrangements of the system, the purified water from water treatment facility 90 may be returned to boiler 22, but preferably to biomaterial cooker facility 30, and/or fermenter 80 and/or composter 40 to make up for water lost during operation.

To supplement fossil fuel feed 84 and to provide oxygen, composter gases conduit 76 from composter 40 and fermenter gases conduit 72 are routed to blower 86. Blower gases 82 are combined with fossil fuel feed 84 to reduce emissions of certain regulated gases upon combustion. Composter gases 76 and fermenter gases 72 are high in volatile organic compounds and water vapor. In embodiments, increased volatile organic compounds in the combustion air reduce fossil fuel consumption. Fossil fuel consumption is also reduced by increased water vapor in stack gas 26b which increases its dew point resulting in more heat transfer into composter 40 out of duct 28 resulting in higher temperature and lower oxygen concentration in ducts 76, 78, and 82, while emissions of oxides of nitrogen (NOx) are reduced.

Water treatment facility 90 is configured to treat the waste liquids and produce clean water. Water treatment facility 90 may comprise conventional systems or devices without limitation as known to one skilled in the art. In embodiments, the water treatment facility 90 comprises at least a trickling filter. Typically a trickling filter is an attached growth bioreactor and a settler for removing organic compounds from water. Filtration and other treatment may occur such that water is of sufficient purity to be discharged.

Energy recovery system 10 utilizes waste heat from the stack gases 26 of stack gas system 20 for preparing biomaterial for composting, enzyme production and/or fermentation. Additionally, by-products of boiler operation are used to generate acidic and/or alkaline chemicals for preparing the biomaterials for enzyme production or fermentation. Heat and combustible by-products from the composting, enzyme production and/or fermentation process, such as volatile organics, dust, mold spores, and/or flying insects, are utilized to reduce fossil fuel consumption by increasing the temperature and amount of fuel in combustion air feed 82 from air blower 86. Non-combustible by-products of the composting, enzyme production and/or fermentation process are utilized to reduce emissions by reducing the oxygen content of the combustion air, leading to lower maximum flame temperature and lower NOx contents in the stack gas. The lowered temperature of stack gases 26b would cause corrosive damage to boiler 22 or boiler stack 32 were these stack gasses not contained in duct 28 and stack 36, constructed of corrosion resistant materials known to those skilled in the art.

The temperature of the stack gases in boiler applications is between about 350° F. and about 700° F., preferably between about 400° F. and about 500° F., and the velocity is from about 5 ft/s to about 50 ft/s. These parameters will vary depending on operating conditions as is known to one skilled in the art. Under typical operating conditions, the heat not recovered from the stack gas is typically released to the environment via stack 32. The burning of the hydrocarbon fuels in burner 24 to heat water in boiler 22 produces stack gases 26a. Burner 24 burns the fossil fuel from feed 84 and the combustion air from feed 82. The properties of the combustion air impacts the stack gases 26a, including temperature, humidity, density, and emissions of monitored compounds, such as oxides of nitrogen (NOx), released to the environment. Additionally, the stack gases 26a contain acidic compounds that would be corrosive to the boiler 22 and boiler stack 32 if they condensed to liquid.

As a result of continued operation, boiler 22 requires extra fuel to minimize condensation of the corrosive components in exhaust gases. Boiler water treatment 60 provides water to boiler 22 and further adds basic or alkaline chemicals to the feed water conduit 95 to minimize corrosion in the steam and or hot water piping. After extended operation, boiler 22 begins to collect solid particulate matter and waste compounds on the waterside of boiler tubes. This material and its precursors, contained in blowdown liquid, are removed from boiler 22 to maintain operational efficiency by blowdown conduit 92. Due to conditions within boiler 22, the compounds contained in the blowdown are typically alkaline. The blowdown liquid may be neutralized in typical operations by adding acidic compounds from the water treatment facility 60 or adding purchased acid by treatment conduit 94 so that the blowdown liquid can be treated and released. Treatment conduit 94 empties into blowdown treatment conduit 96, which feeds the basic water treatment/storage facility 98. The wastewater generally resultant from boiler operation may be considered boiler operation wastewater.

In energy recovery system 10, the blowdown liquid may be combined with wastewater from the water treatment facility 60 from conduit 94 and the resulting stream in blowdown treatment conduit 96 are introduced to basic water treatment/storage facility 98. Treated basic water stream is transported by conduit 99 to cooking vessel 38 to make up for cooking liquor lost during the biomaterial cooker process.

Figure 2:
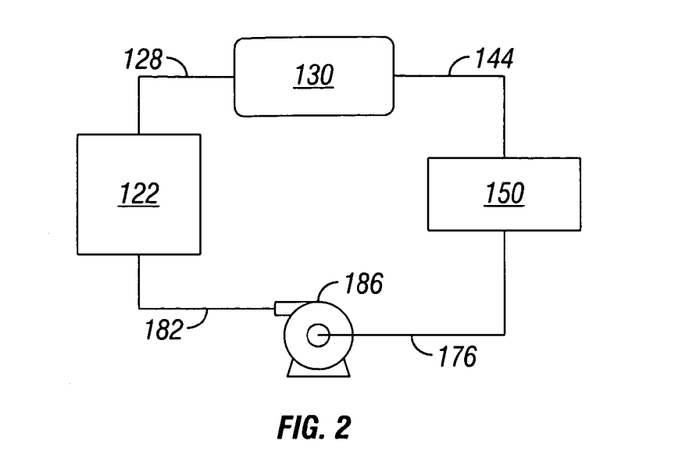
FIG. 2 is a thermal energy flow diagram according to an embodiment of an energy recovery and recycling system.

In addition to controlling emissions and reducing corrosion, the heat energy in the stack gases is recovered for additional processes by energy recovery system 10. FIG. 2 illustrates a flow diagram of an embodiment of gas cycle 100 in energy recovery system 10 whereby thermal energy in the boiler stack gas conduit 128 is recovered and recycled. In boiler 122, water is heated to boiling by burning hydrocarbon fuels. Rather than being released to the environment, the heat from high temperature boiler gas conduit 128 is cycled to a biomaterial cooker facility 130. Biomaterial cooker facility 130 acts to exchange the heat from high temperature boiler gas conduit 128 to cook the biomaterials. Biomaterial cooker facility 130 utilizes the high temperature to further the dissolution of biomaterial into cellulose, hemi-cellulose, and lignin.

From biomaterial cooker facility 130, hot gases in conduit 144 are transported to bioreactor 150. In embodiments, bioreactor 150 comprises composters, fermenters, and/or other processes that utilize bacteria, fungi, enzymes or multi-cellular organisms to break down, digest, or alter biomaterial. The units of bioreactor 150 further act as heat exchanger whereby the hot gases exchange heat with the biomaterials. Heating biomaterials, undergoing aerobic composting and anaerobic fermentation is advantageous for the release of organic volatile gases and water vapor. Bioreactor gas conduit 176 exits bioreactor 150 at an elevated temperature, advantageous for introduction as combustion air into burner 122. Bioreactor gas conduit 176 may be combined with fermenter gas and introduced to burner 122 via blower 186. The heated bioreactor-gases in conduit 176 are mixed with combustion air or fuel in blower 186 for burner gas feed 182. The temperature and humidity is elevated in burner gas feed 182, thus reducing the emissions produced in boiler 122.

In certain embodiments, the hot gas conduit 144 may leak into the bioreactor facility as a means to recycle stack gases. It is advantageous to recycle some of the hot gases as means to further reduce NOx emissions. Additionally, this method may reduce costs to construct the bioreactor 150.

Figure 3:
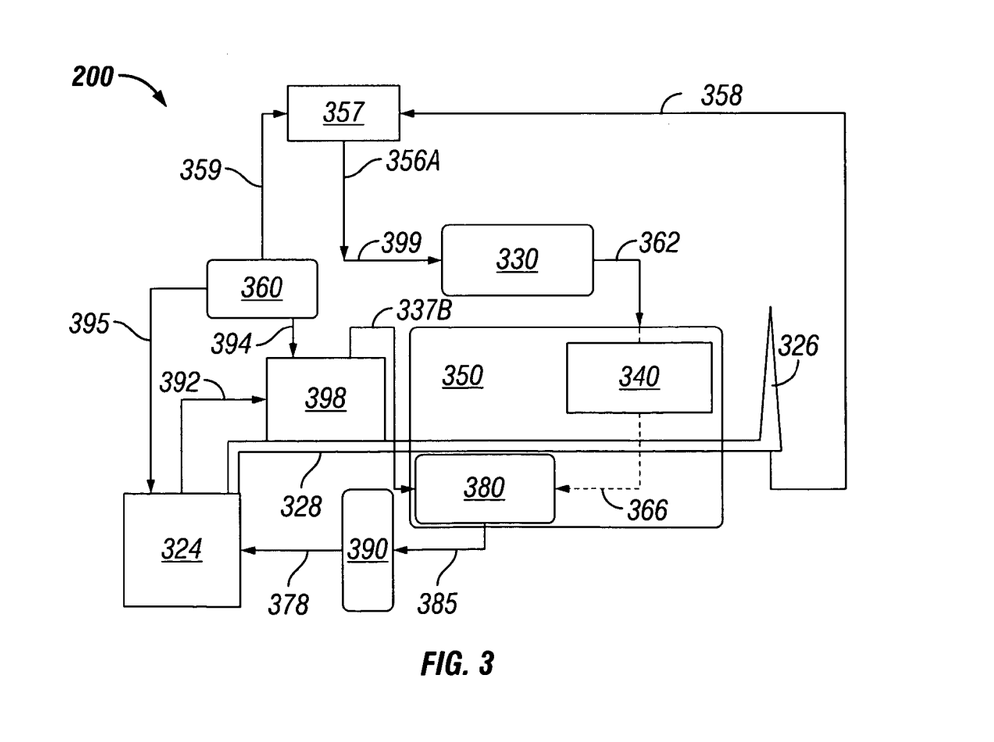
FIG. 3 is an acidic liquid flow schematic according to an embodiment of an energy recovery and recycling system.

Referring now to FIG. 3, an embodiment of an acidic cooking liquor water cycle 200 for energy recovery system 10. Feed water conduit 395 to boiler 324 is de-mineralized by boiler water treatment 360. Boiler water demineralizer 360 uses acidic chemicals like hydrochloric or sulfuric acid and basic chemicals like caustic soda and/or caustic potash to regenerate ion exchange resins for demineralization. An acidic wastewater stream 359 and a basic wastewater stream 394 result. The acidic wastewater stream 359 is combined with the acidic condensate 358 from gas conduit 328. Gas conduit 328 exhausts combustion products from boiler 324 to stack 326 through bioreactor 350. A portion of the chemicals from demineralizer regeneration are highly acidic. The chemicals from condensation in the stack may also be highly acidic if the fuel fired in boiler 324 contains sulfur. The combined acidic streams 358 and 359 are stored in acidic water treatment/storage facility 357. Conduit 356A routes this acidic water to biomaterial cooker facility 330 via conduit 399. Biomaterial cooker facility 330 heats cellulose containing biomaterial in a solution, or cooking liquor. Heating the cooking liquor dissolves the lignin hemicellulose and leaves the cellulose unsolubilized. Biomaterial outlet stream 362 enters bioreactor 350, comprising, for example, composter 340 and fermenter 380. The remaining cellulose, hereinafter called pulp, is strained from the cooking liquor in bioreactor 350. The de-lignified cellulosic pulp is used for further processes such as but not limited to: ethanol or other fermentation, enzyme production, animal feed, biofuel, or other applications as known to one skilled in the art.

Although demineralizing removes many minerals, salts and other chemicals from the boiler feed water in conduit 395, residual compounds remain. As the water boils within boiler 324, the concentrations of these materials increase, reducing the efficiency of boiler 324. In order to return to optimum efficiency, these materials are removed and in blowdown via conduit 392. The residual compounds are stored with basic wastewater from conduit 394 originating in demineralizer 360 in the basic water treatment/storage facility 398. The basic water stream from water treatment/storage facility 398 is routed to fermenter 380 via conduit 337B. In certain embodiments, bioreactor 350 comprises composter 340 and fermenter 380. In further embodiments, bioreactor cooking liquor is drained from composter 340 to fermenter 380 by conduit 366.

Figure 4:
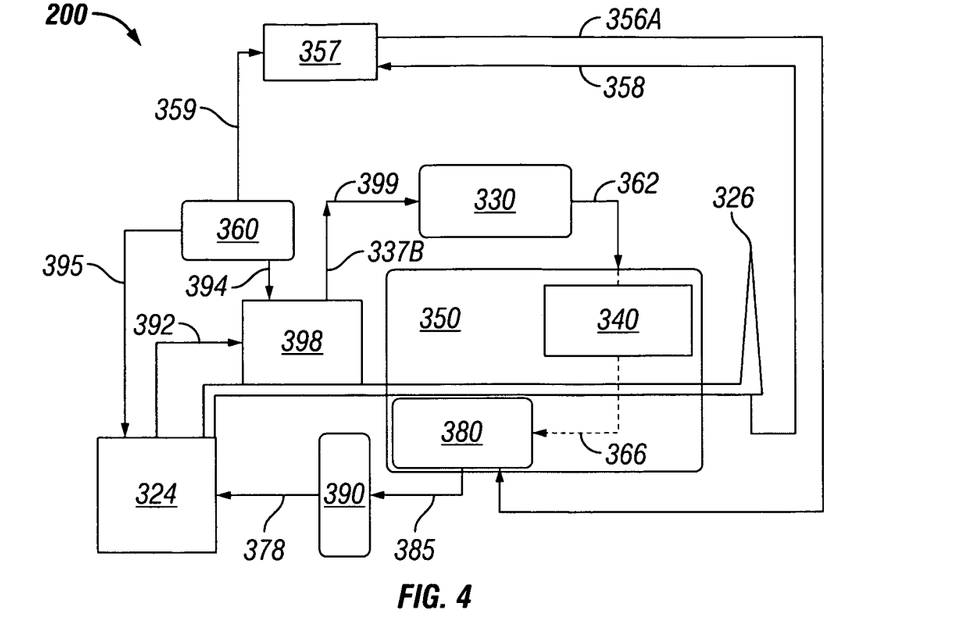
FIG. 4 is a basic liquid flow schematic according to an embodiment of an energy recovery and recycling system.

Referring now to FIG. 4, an embodiment of a basic cooking liquor water cycle 200 for energy recovery system 10. Feed water conduit 395 to boiler 324 is de-mineralized by boiler water treatment 360. Boiler water treatment 360 uses acidic chemicals like hydrochloric or sulfuric acid and basic chemicals like caustic soda and/or caustic potash to regenerate ion exchange resins for demineralization. An acidic wastewater stream 359 and a basic wastewater stream 394 result. The acidic wastewater stream 359 is combined with the acidic condensate 358 from gas conduit 328. Gas conduit 328 exhausts combustion products from boiler 324 to stack 326. The combined acidic streams 358 and 359 are stored in acidic water treatment facility 357.

Although demineralizing removes many minerals, salts and other chemicals from the boiler feed water in conduit 395, residual compounds remain. As the water boils within boiler 324, the concentrations of these materials increase, reducing the efficiency of boiler 324. In order to return to optimum efficiency, these materials are removed and in blowdown via conduit 392. The residual materials may be stored along with basic wastewater from conduit 394 originating in demineralizer 360 in the basic water treatment/storage facility 398. The caustic chemicals from ion exchange resin regeneration and the use of basic chemicals to protect the boiler and associated lines from corrosion leaves the basic water treatment facility 398 in conduit 337B as a highly basic liquid mixture. This basic water is routed to biomaterial cooker facility 330 via conduit 399.

Biomaterial cooker facility 330 heats cellulose containing biomaterial in a solution, or cooking liquor, to dissolve the lignin and leave the cellulose unsolubilized. In certain basic cooking liquor embodiments, the nitrogenous-basic compounds concentrations in the cooking liquor are supplemented by the addition of lime or potash to both supply additional base for cooking liquor and improve compost quality. Biomaterial outlet stream 362 enters bioreactor 350, comprising, for example, composter 340 and fermenter 380. The remaining cellulose, hereinafter called pulp, is strained from the cooking liquor in bioreactor 350. The de-lignified cellulosic pulp is used for further processes such as but not limited to ethanol or other fermentation, enzyme production, animal feed, biofuels, or other applications as known to one skilled in the art.

The cooking liquor within 362 has a high nitrogen content resulting from corrosion inhibitors in the boiler blowdown and from cooking the biomaterial. The high nitrogen content is advantageous for many processes within bioreactor 350 such as but no limited to, composting and fermenting. In certain embodiments, bioreactor 350 comprises composter 340 and fermenter 380. In further embodiments, bioreactor cooking liquor is drained from composter 340 to fermenter 380 by conduit 366. The cooking liquor may combine with the acidic water stream from conduit 356A draining acidic water treatment facility 357.

In either acid or basic cooking liquor applications, waste water from fermenter 380 is removed by conduit 385 to water treatment facility 390. Water treatment facility 390 treats the waste water for biological material and removal of organic compounds. In some embodiments, water treatment facility 390 comprises a trickling filter and treats the waste water in preparation for release as water of sufficient purity to discharge. Alternatively, water treatment facility 390 removes organic material as sludge from waste water. In further embodiments the sludge may be returned to the fermenter 380. Water treatment facility 390 also humidifies the air surrounding filters and treatment apparatuses. The humid air from water treatment facility 390 may be returned to boiler 324 in the combustion air feed 378 for reducing regulated emissions.

Water may be routed to alternative facilities as a means to regulate the humidity of the processes conducted therein. In these embodiments, the water in biomaterial cooker 330 is sourced from boiler blowdown treatment 398, boiler water treatment 360, water treatment facility 390 and/or condensate from stack gas conduit 328. In further embodiments the hot water in the cooking liquor from biomaterial cooker facility 330 may additionally be used to produce steam, and to condense this steam to water for treatment in water treatment facility 390. Further, water for fermenter 380 may be sourced from boiler 324 feed water excesses. Water from fermenter 380 may be routed (not shown in Figures) to composter 340 to increase the moisture and nitrogen in the biomaterial as needed.

Referring again to FIG. 1 In further alternative embodiments, the cooking liquor for pulping in biomaterial cooker facility 30 may be provided from biofuel waste products. The biofuel waste byproducts such as glycerol, methanol, butanol, and spent enzymes, monobasic and dibasic acids are feasible additives for the heated delignification of cellulose. Further, the spent catalyst utilized in fatty acid ester biofuel production mixed with the soda or potash is envisioned as a component of the cooking liquor, in some embodiments.

In further alternative embodiments, the cooking liquor for biomaterial cooker facility 30 may be provided from boiler operation wastewater. The wastewater may be derived from solid fuel handling waste products. Storage of coal or peat or other solid fuels results in fuel pile runoff, the water-soluble components of which are known to those skilled in the art to promote the hydrolysis of lignin. Acid mine drainage potentially available to power plants located near mines is also a promoter. Additionally in cold weather, the contents of fuel piles are sometimes treated with antifreeze components such as glycols, known to those skilled in the art both to promote the hydrolysis of lignin and to solubilize the resulting hydrolysis products. These antifreeze components are contained in runoff. Also most solid fuels contain ash precursors. Collection of ash sometimes involves contacting ash with water. This contacting makes available the water-soluble portions of the ash to promote the hydrolysis of lignin. Any of these aqueous streams are envisioned as a component of the cooking liquor, in some embodiments.

Figure 5:
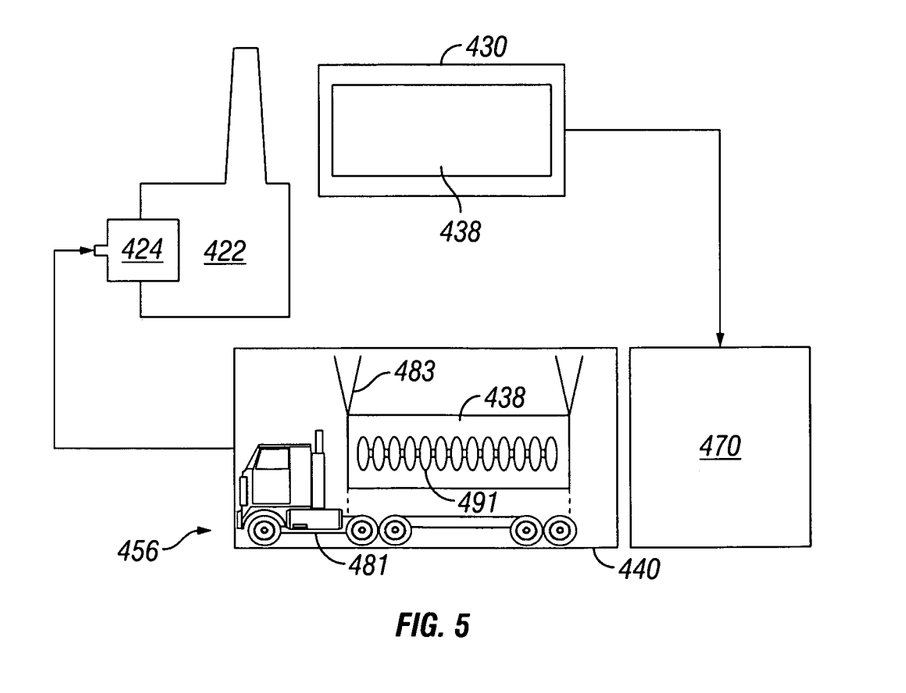
FIG. 5 is an illustration for transporting and agitating biomaterial.

Referring to FIG. 5, in another embodiment, vessel 438 is a commercial biomass transport to move biomass into, out of, or about the energy recovery and recycling system 10. A trailer, or rail car attachment are potential examples of commercial transports to move biomaterial about the energy recovery and recycling system 10. For example, the biomaterial may be transported from the biomaterial cooker facility 430 to the biomaterial separator 470. In further applications, vessel 438 may be transported to a commercial garage bay 456 of composter 440. It can be envisioned that a ceiling-mounted lift system 483 removes and suspends the vessel 438 above the transporter 481 from the ceiling of the composter 440. In order to distribute heat through the biomass contained therein, an agitator 491 may be employed to agitate the contents of vessel 438 after the tractor-trailer 456 is driven out from under vessel 438. Alternatively, the lift system 481 may agitate the compost. Furthermore, agitation of the biomass prevents caking along the walls of vessel 438. In certain embodiments, vessel 438 comprises an agitator 491 disposed within said vessel; the internal agitator may act on the compost by mixing, turning, stirring and/or other actions. Vessel 438 may further serve to transport compost to burner 424 and boiler 422 for fuel.

The following examples are provided to further illustrate various embodiments of the present invention.

EXAMPLES

In the following examples, all gas rates are in SCF (standard cubic feet) per stream hour unless otherwise noted, and all liquid and solid rates are in lbs per stream hour unless otherwise noted. The flue gas system has 10 MM BTU/H (Million British Thermal Units per Hour) fuel fired with 15% excess combustion air having an ambient humidity of 100% at 70° F. The stack gas exits from the flue gas system at a temperature of substantially 460° F., unless otherwise noted.

Figure 6:
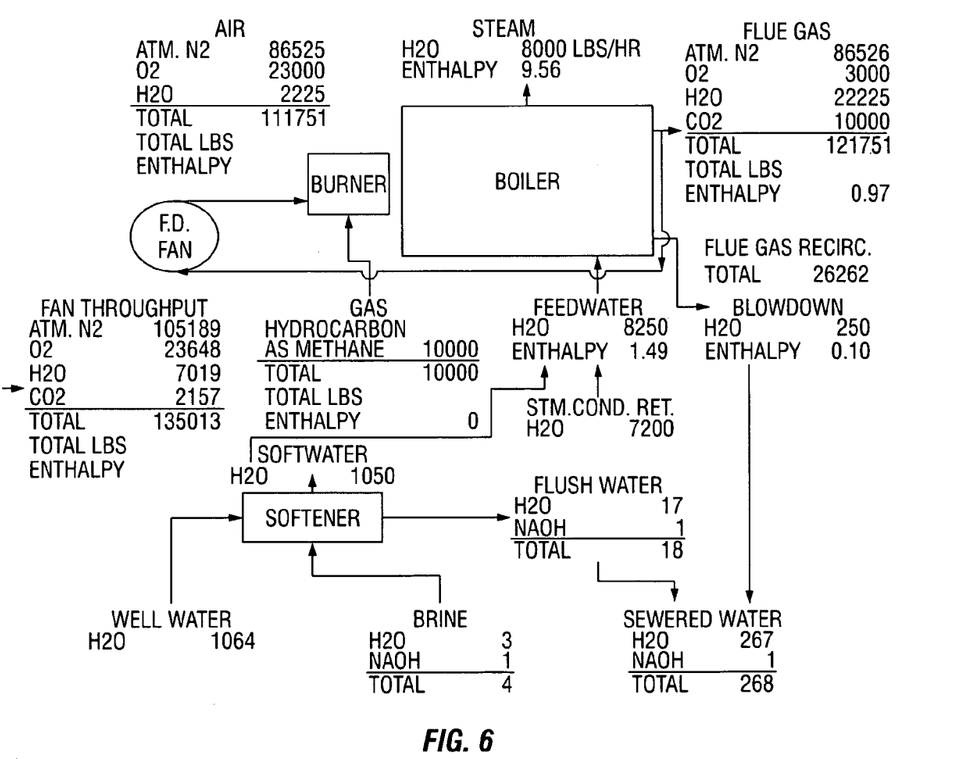
FIG. 6 a conventional boiler material flow diagram.
Figure 7:
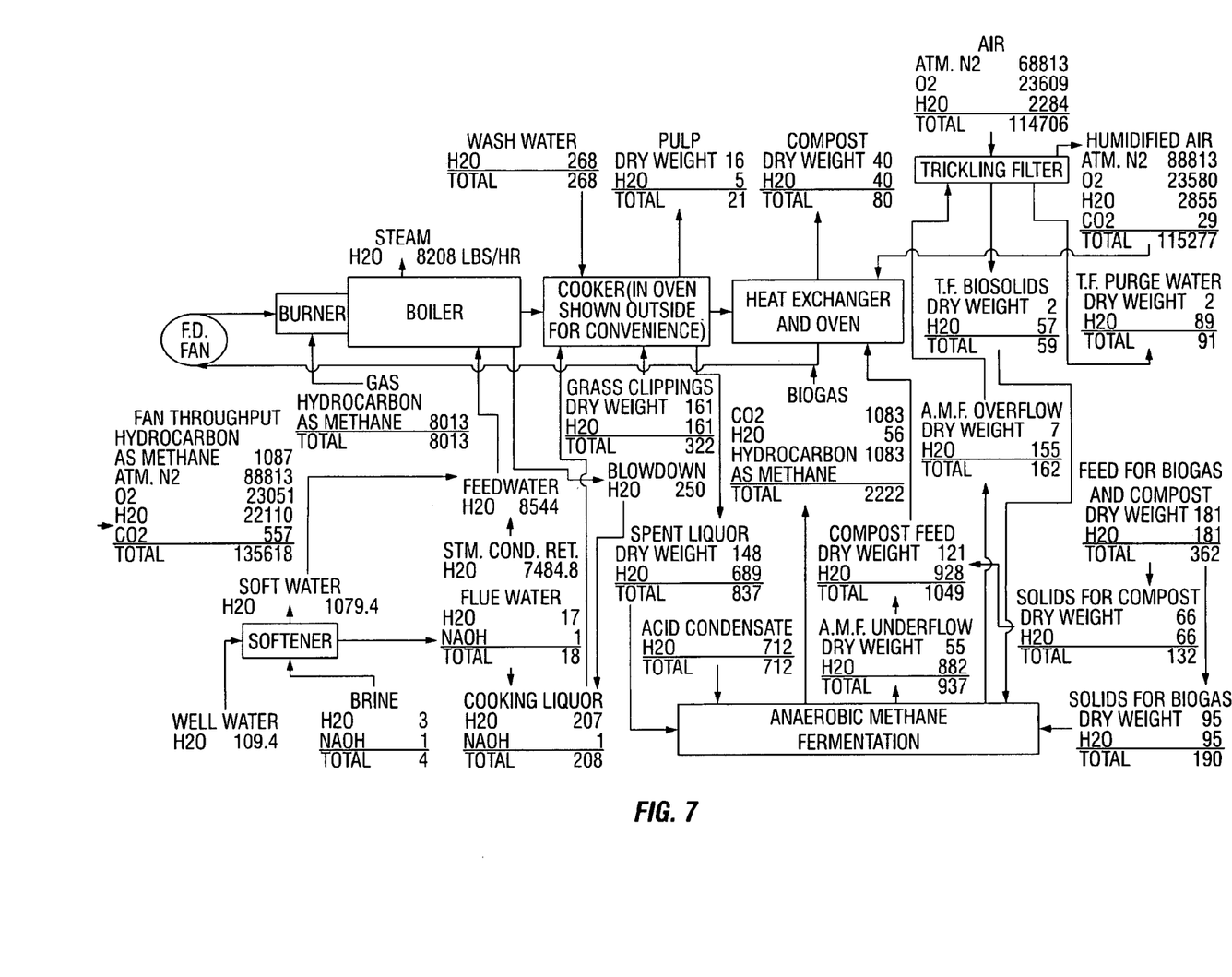
FIG. 7 is a material flow diagram of an example of an energy recovery system with an open composting system.

Illustrated in FIG. 6 is a conventional boiler application, without biomaterial incorporation for recovery and recycling. Illustrated in FIGS. 6 and 7 are specific embodiments of an energy recycling system with biomaterial treatment and bioreactor facilities for the production of pulp and compost.

Example Calculations 1

Conventional Boiler System

In a standard boiler system illustrated in FIG. 6, the calculations for gaseous fossil fuel flow and oxygen mixture are 10 MMBtu/H*1000 Btu/SCF (Btu per standard cubic foot)= 10000 SCF/H (standard cubic feet per hour) of fuel gas. @2 volumes O2 per volume fuel gas=20000 SCFH O2 are required. @4.762 volumes air per volume O2 plus excess Air @15%, 109526 DSCF/H (dry standard cubic feet per hour) air are required.

Adding relative humidity to the air, at 70° F. and 100% relative humidity, moisture is equal to 0.0158 lbs H2O per lb. dry air. In other units, moist air is comprised of 1 lb. dry air=13.35 CF (cubic feet) dry air and of 0.34 CF H2O=0.0158 lbs H2O. This composition is equivalent to 13.69 CF of moist air weighing 1.01 lbs. The burner feed is thus 109526 DSCF/H Air+2781.64 SCF (standard cubic feet) H2O. This humid air is fed to the burner along with 10000 SCF/H (standard cubic feet per hour) of fuel gas. Enthalpy of the humid air is 34.09 Btu/lb dry air=301611.42 Btu/H, calculated using 359 SCF per lb mole and 29 as MW (molecular weight) of air.

After combustion, the stack contains 10,000 SCF/H CO2 and 22781.64 SCF/H H2O and CF/H Atm Nitrogen and 3000 CF/H O2 totaling 122307.64 CF/H. The stack contains 22781.64 SCF/H water in 122307.64 total SCF/H which provides a flue gas composition of 0.23 moles water per mole dry gas. This composition is equivalent to 0.14 lbs H2O per lb dry air for a dew point of 137° F. This 137° F. dew point forms the design goal for the exit temperature of the high temperature side of a heat exchanger, the low temperature side of which contains biological material. Any water vaporized in the low temperature side will be condensed in the high temperature side if this goal is met. This cycle maximizes the utilization of the biologically derived heat. Much of this biological heat vaporizes water, present in large amounts during biological processes from biological necessity. The heat of vaporization of this water is recovered for preheating combustion air in the process of this invention.

Example Calculations 2

Energy Recycled via Biomaterial and Bioreactors

Using biomass in the flue gas system alters the material and energy balances and the water usage. Below is an heat transfer calculation using the equation $Q=UA(\Delta T)$.

Extremophile bacteria in composting do well between 70° F. and 158° F., therefore assume the average temperature of 70° F.+158° F./2=114° F. to be the low temperature side of a biomaterial heat exchanger. The stack temperature as set forth above is 460° F. The average high side temperature can be assumed to be 298.5° F. because the high side temperature decreases down to 137° F. from 460° F. The average $\Delta T$ is 298.5° F.−114° F.=184.5° F. Typical tubular heat exchangers have heat transfer coefficients, U, of 10 to 50 with air on the shell side and 5 to 20 with air on the tube side.

Window glass has a heat transfer coefficient, U, of about 1.2 at standard conditions which are at low temperature, no wind, and no condensation. Radiant heat varies as the fourth power of the temperature and its contribution to the U rises quickly with temperature. Use 3.1 for the heat transfer coefficient, Q. The heat flow for an exchanger in the stack above going from 460° F. to 137° F. is 808130.51 Btu/H.

Solving for A in $Q=UA(\Delta T)$, The area of the heat exchanger/composter is 1412.94 square feet. This is less than the surface area of a building needed for composting 1 MM Btu/H of biomass. Such a building roughed out below is a 44100 gallon tank. If diameter D equals height, H=19.5 feet, the outside area of a tank this size is 1792.436 square feet. So a double walled building containing the same volume as the tank would be large enough to furnish the calculated heat exchanger area.

To calculate the heat of Combustion or heat of Bacterial Metabolism of biomass use publised values for Bagasse, which is sugarcane pulp, and is primarily composed of carbohydrates. As an example for a burner, using the carbohydrate formula $CH_2O$, gives a molecular weight, MW, of 30. The use of the molecular weight of monomeric carbohydrate creates very little error when calculating the combustion stoicheometry of polymeric carbohydrates, like bagasse. Bagasse combustion produces 8000 Btu/lb, on a dry basis. So, 1 MMBtu/H requires 125 lb/Hr of dry bagasse. Using the MW of 30, 4.17 moles/hr $O_2$ are required. At 359 SCF per mole, the $O_2$ required=1495.83 SCFH $O_2$. At 4.76 volumes of air per volume $O_2$ in atmospheric air, the air required is 8191.63 DCF/H air. Enthalpy is 34.09 Btu/lb dry air=22558.02 Btu/H.

Flue Gas from the above calculation contains 1495.83 CF/H $CO_2$, 1703.87 CF/H $H_2O$ and 6471.42 CF/H Atmospheric Nitrogen and 224.375 CFH $O_2$ with 15% excess air. The total flue gas is 9895.508815 CFH.

In the system, the biological zone replaces flue gas recirculation, and the assumption is made that the dry basis heat capacities of air and flue gas are the same. The error in this assumption is about 3.0%, based on the approximation that all heat is quenched by water. Quenched by water is the same thing as saying all temperature rises result in 100% relative humidity. This approximation is justified by the large amounts of water known to be present because water is required to support bacterial life.

Fifteen percent (15%) is a poor (low air) assumption for in-vessel composting excess air, as is saturation equilibrium between water and air. Particularly since, if plant matter did not preferentially absorb water life would not exist. It is thought that the combination of these two bad assumptions will result in a good assumption based on billions of years of evolution requiring it to be good. If it weren't, there would be an excess of partially decayed fern trees not eaten by dinosaurs. Another way of justifying the combination these two poor assumptions is that in the adiabatic system of this invention the biological heat will get to the boiler in some combination of hotter air with increased moisture content. For economics purposes in the condensing air preheater system of this invention it really doesn't matter much exactly what this combination is.

Proceeding with the 1 MM Btu/H of biomass calculation, the dry basis incoming air plus flue gas from biological material is: 117717.63 CF/H=9509.22 lbs/hr. Enthalpy is 1324169.44 Btu/H or 139.25 Btu/lb which puts the temperature at 125° F.; At 125° F. and water saturation, water content increases the total volume of 1 lb of dry air plus water to 17 cubic feet. Dry air alone is 14.73 CF per lb of dry air. The difference of 17−14.73=2.27 cubic feet of water weighs 0.095 lbs. The humid air thus contains 0.095 lbs. $H_2O$ per lb dry air.

Incoming $O_2$ in the combustible mixture in the burner is 17.09% percent. This is near ideal for flue gas recirculation. A 23.5%, basis incoming air, flue gas recirculation would achieve the same $O_2$ percentage of 17%. A 21.00%, basis incoming air, flue gas recirculation would achieve the same temperature: 125.54 or 125° F. assuming 460° F. stack temperature. However steam generation would of course be higher with the biomass. If the biomass is 50% water, then 6000 pounds per day would be required, however biomass is and must be much wetter than this. In this example, water flows out of the biological zone at 903.38 lbs per hour. Water in is 139.47 lbs per hour from incoming air+85.43 lbs/hr from oxidation. The difference between 903.38 lbs per hour of water leaving and (85.43+139.47)=224.9 lbs. per hour of water available from other sources is the amount of water evaporated from the biomass, which is 678.48 lbs per hour. Dry basis biomass is 125 lbs/hr, meaning the biomass must either contain initially 84% water or be contacted later with makeup water if it is dryer than 84%. The 678.48 lbs per hour of water evaporated from the 1 MMBtu per hour of incoming biomass can be expressed as 0.68 lbs water per MBtu of biomass combusted or oxidized.

Another source of heat, which will also cause water to evaporate is heat input through the exchanger. 808130.51 Btu/H, a number derived in example 1 from calculating the heat exchanger with no biomass, gives an enthalpy of 1109742 Btu/H leaving the heat exchanger. This enthalpy is 125.43 Btu per lb dry air.

The resulting temperature is 122° F., which at saturation gives 14.66 CF dry Air and 2.03 CF of $H_2O$. This totals 16.6 CF of humid Air containing 18.44% $O_2$. Water is used at the rate of 622.35 lbs per hour which can be expressed as 0.77 lbs $H_2O$ per Mbtu of heat exchanged. Repeating this heat exchanger calculation for 1 MM Btu/H transferred gives 1301611.42 Btu/H Enthalpy leaving the heat exchanger. This enthalpy is 147.12 Btu/Lb dry air at a temperature of 128° F. with an $O_2$ content of 17.99%. This compares to an oxygen content of 17.09% for the same number of Btu from oxidation of biomass. So one comparison is that 1000 Btu of Heat transfer is as good at reducing the oxygen content of the incoming air as is 771.72 Btu of biomass oxidation. This same estimation technique for the 808130.51 BtuH of heat transfer yields the result that 1000 Btu of heat transfer and is as good as 810.66 Btu of oxidation for reducing the oxygen content of the incoming air.

Using 800 Btu of heat transferred as equivalent to 1000 Btu of biomass oxidation for reducing incoming air oxygen content as an engineering approximation for comparing indirect heat transfer to oxidation of biomass, conventional composting with a 49 day residence time would require an inventory of 294000 lbs which at 50 lbs per CF would occupy 5880 CF=44100 gal. That amount could be handled in a reasonably sized tank or airtight enclosed building. This size would be greatly reduced if the compost were consolidated as its volume shrank. In-vessel composting can take 7 to 14 days because of better air contacting and temperature control. In-vessel composting is preferable, especially if the agricultural operation which produces the biomass will take back its compost, because the compost so returned does not have to be completely stabilized.

To compare the size of potential water sources, boiler blowdown at 4 cycles and 1000 Btu/lb heat of vaporization and 90% condensate return is 250 lbs/H=719.42 gal/day compared to approximately 900 gal/day needed based on 6000 lbs/Day of 50% water biomass. This is close. Adding the regeneration caustic water would not increase the water volume much. A provision can be made for recycle of some trickling filter water to smooth out operations and for tank storage of blowdown and regeneration water until needed. Cooling tower blowdown condensing the boiler's steam generated at 70% efficiency assuming 3 cycles of concentration in the cooling tower is 2333.33 lbs/H, which is plenty of water.

TABLE 1

Enthalpy Balance around the boiler. (FIG. 6)

Enthalpy Balance MMBtu/H

| IN | OUT | |
|---|---|---|
| 1.49 | | FEEDWATER |
| | 0.10 | BLOWDOWN |
| | 9.56 | STEAM |
| | 0.97 | STACK |
| 9.56 | | FUEL(LHV) |
| | 0.41 | LOSS |
| 11.05 | 11.05 | TOTAL |

TABLE 2

Enthalpy Considerations. (FIG. 7) expressed in lbs of steam for consistent units

| Enthalpy Considerations | lbs steam/H |
|---|---|
| EVAPORATED in composter | 938 |
| CONDENSED water in exchanger | 712 |
| COOLED OFF gas in exchanger | 741 |
| INCREASED STEAM MAKE from boiler | 514 |
| ASSUME half of this increased STEAM MAKE is lost | 257 |

TABLE 3

Enthalpy fates. (FIG. 7)

| USED | 2576849 | Btu Biofuel |
|---|---|---|
| SAVED | 1408968 | Btu Fossil Fuel |
| Produced | 128884.9 | Btu PULP |
| Produced | 320276 | Btu Compost |

TABLE 4

Figure 8A:
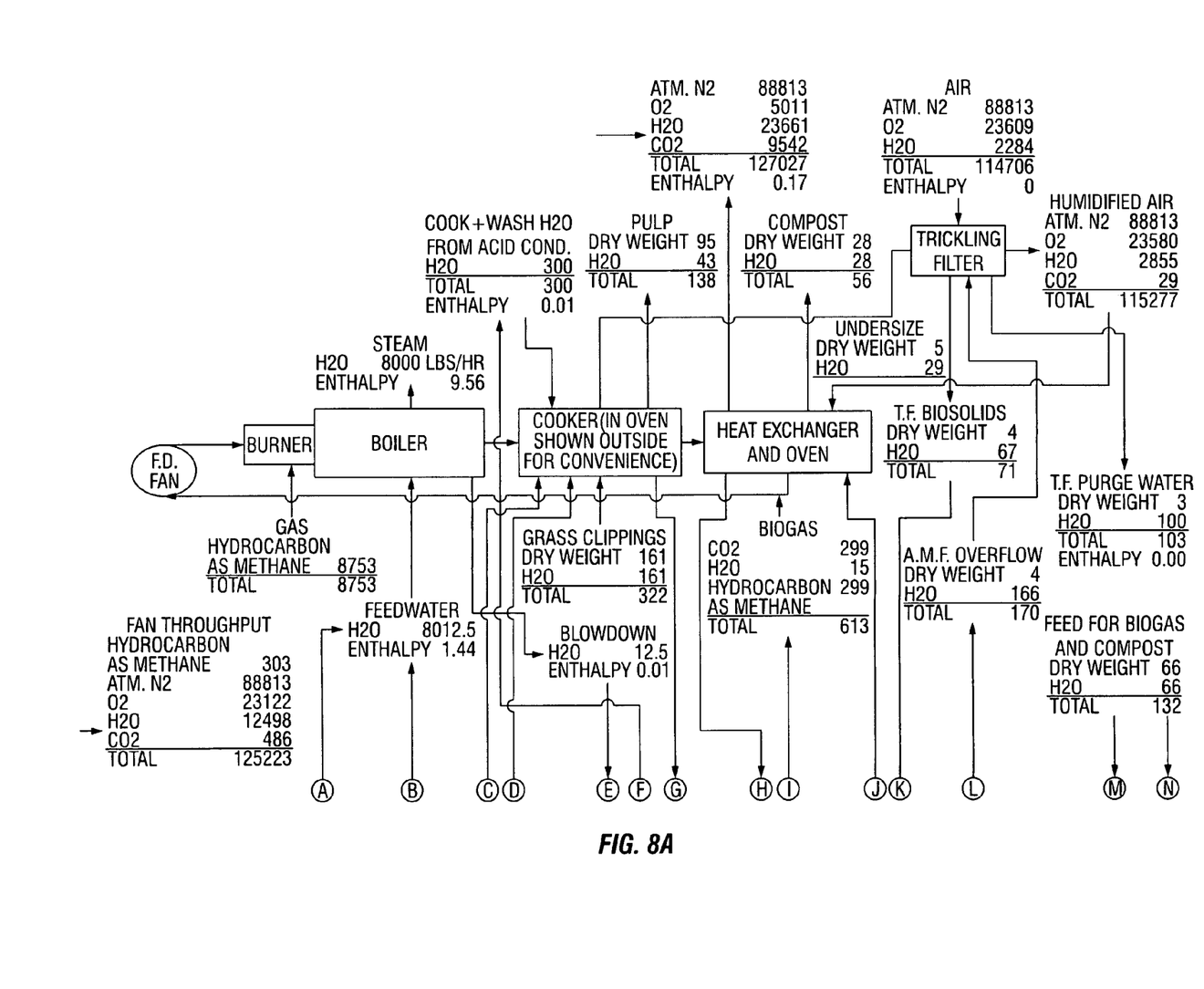
FIG. 8A is a material flow diagram according to an example of an energy recovery system with demineralized feedwater.
Figure 8B:
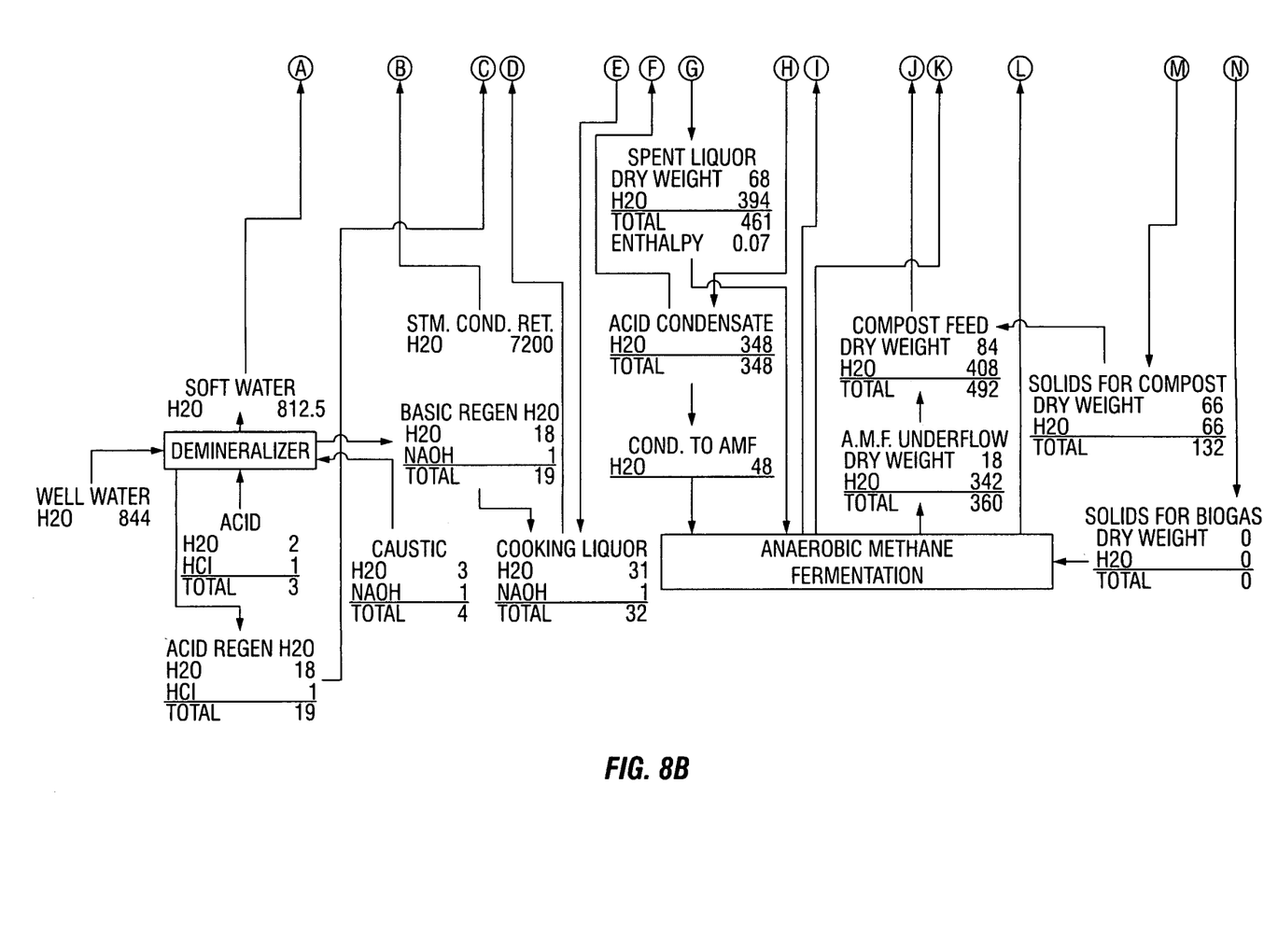
FIG. 8B is a material flow diagram according to an example of an energy recovery system with demineralized feedwater.

Enthalpy Balance. (FIG. 8A and 8B)

Enthalpy Balance MMBtu/H

| IN | OUT | |
|---|---|---|
| 1.44 | | FEEDWATER |
| | 0.01 | BLOWDOWN |
| | 9.56 | STEAM |
| | 0.17 | STACK |
| 0.45 | | BIOSOLIDS HEAT OF COMB |
| 8.66 | | FUEL(LHV) |
| | 0.82 | LOSS |
| | 0.00 | T. F PURGE WATER |
| 0.01 | | WASH WATER |
| 10.56 | 10.57 | TOTAL |

Fuel saved is about 9% of the fired duty.

TABLE 5

Fermenter Water Balance Calculations: Anaerobic Methane Fermenter. (FIG. 8A and 8B)

FERMENTER WATER BALANCE

| IN | OUT | |
|---|---|---|
| 394 | | SPENT LIQUOR |
| 48 | | ACID CONDENSATE |
| | 342 | A. M. F. UNDERFLOW |
| | 166 | A. M. F. OVERFLOW |
| 67 | | T. F. BIOSOLIDS |
| | 1 | BIOGAS |
| 509 | 509 | TOTAL |

TABLE 6

Heat Exchanger Water Balance Calculations. (FIG. 8A and 8B)

HEAT EX WATER BALANCE

| IN | OUT | |
|---|---|---|
| 408 | | COMPOST FEED |
| 143 | | HUMIDIFIED AIR |
| 42 | | COOKER VENT |
| 1 | | BIOGAS |
| 34 | | COMPOST REACTION |
| | 627 | FAN THROUGHPUT |
| 627 | 627 | TOTAL |

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

What is claimed is:

1. A method of recycling thermal energy from a boiler, comprising:
    coupling a thermal gas conduit from a burner component of the boiler to a biomaterial cooker and a bioreactor, wherein the bioreactor comprises an anaerobic fermenter and an aerobic composter;
directing a combustion gas through the thermal conduit from the burner through the biomaterial cooker and the bioreactor to form a thermal gas cycle;
recovering liquid by-products from the conduit and the boiler;
directing an acidic portion of the liquid by-products through the biomaterial cooker and a basic portion of the liquid by-products through the bioreactor to form a thermal liquid cycle;
recovering the acidic portion and the basic portion of the liquid by-products from the biomaterial cooker and the bioreactor; and
returning thermal energy to the burner and the boiler from the thermal gas cycle and the thermal liquid cycle to reduce emissions and fossil fuel consumption in the operation of said boiler.

2. The method of claim 1, wherein the thermal gas conduit comprises a burner combustion gas exhaust stack.

3. The method of claim 1, wherein directing the acidic portion of the liquid by-products through the biomaterial cooker comprises directing boiler steam and condensate water from the thermal conduit to the biomaterial cooker.

4. The method of claim 1, wherein directing a basic portion of the liquid by-products through the bioreactor comprises directing boiler blowdown and boiler treatment water waste to the bioreactor.

5. The method of claim 3, wherein directing the acidic portion of the liquid by-products through the biomaterial cooker comprises dissolving hemicellulose.

6. The method of claim 2, further comprising:
removing the biomaterial from the biomaterial cooker and placing it into the aerobic composter; separating the acidic portion of the liquid by-products; and directing the thermal gas through the cooked biomaterial.

7. The method of claim 4, wherein directing the basic portion of the liquid by-products through the bioreactor comprises introducing the basic portion of the liquid by-products to the anaerobic fermenter.

8. The method of claim 1, wherein returning thermal energy to the burner and the boiler comprises recovering the thermal energy from at least one biomaterial cooker product selected from the group consisting of pulp, food products, fuel products, pyrolysis products, cooking liquor, vent gas, or combinations thereof.

9. The method of claim 1, wherein returning thermal energy to the burner and the boiler comprises recovering thermal energy from at least one bioreactor product selected from the group consisting of compost, pulp, enzymes, water, gases, or combinations thereof.

10. The method of claim 1, wherein returning thermal energy to the burner and the boiler comprises heating combustion air fed to the burner.

11. The method of claim 10, wherein heating the combustion air further comprises releasing volatile organic gases from the bioreactor into the combustion air.

12. The method of claim 10, wherein the heating the combustion air further comprises releasing finely divided organic solids from the bioreactor into the combustion air.

* * * * *